US 8,336,366 B2

(12) United States Patent
Roques et al.

(10) Patent No.: US 8,336,366 B2
(45) Date of Patent: Dec. 25, 2012

(54) TRANS-CONFIGURABLE MODULAR CHROMATOGRAPHIC ASSEMBLY

(75) Inventors: Ned Roques, Lewisburg, WV (US); John Crandall, Lewisburg, WV (US)

(73) Assignee: Falcon Analytical, Lewisburg, WV (US)

( * ) Notice: Subject to any disclaimer, the term of this patent is extended or adjusted under 35 U.S.C. 154(b) by 365 days.

(21) Appl. No.: 12/817,137

(22) Filed: Jun. 16, 2010

(65) Prior Publication Data

US 2010/0256922 A1  Oct. 7, 2010

Related U.S. Application Data

(63) Continuation-in-part of application No. 12/555,783, filed on Sep. 8, 2009.

(60) Provisional application No. 61/095,075, filed on Sep. 8, 2008.

(51) Int. Cl.
*G01N 30/02* (2006.01)
(52) U.S. Cl. ....................................... 73/23.39
(58) Field of Classification Search ............ 73/23.39
See application file for complete search history.

(56) References Cited

U.S. PATENT DOCUMENTS

| | | | | |
|---|---|---|---|---|
| 5,611,846 | A | * | 3/1997 | Overton et al. ............ 96/102 |
| 5,808,178 | A | * | 9/1998 | Rounbehler et al. ...... 73/23.39 |
| 6,071,408 | A | * | 6/2000 | Allington et al. .......... 210/634 |
| 6,209,386 | B1 | | 4/2001 | Mustacich |
| 6,530,260 | B1 | | 3/2003 | Mustacich |
| 7,291,203 | B2 | * | 11/2007 | Crnko et al. ................ 95/87 |
| 8,104,326 | B2 | * | 1/2012 | Tipler et al. ............. 73/23.42 |
| 2001/0009647 | A1 | | 7/2001 | Mustacich |
| 2006/0283324 | A1 | | 12/2006 | Roques |

\* cited by examiner

*Primary Examiner* — Hezron E Williams
*Assistant Examiner* — Rodney T Frank
(74) *Attorney, Agent, or Firm* — Sheldon H. Parker, Esq.

(57) ABSTRACT

A trans-configurable modular chromatograph assembly is provided with a core unit, at least one column module, and at least one detector module. The core unit includes a controller module having a first computer processing unit, an analogue to digital signal converter, and a thermally insulated enclosure. The enclosure includes a first heater member positioned to heat the thermally insulated first enclosure housing, a first analytes stream inlet, and a first analyte stream conduit. A temperature controller is programmed to maintain the thermally insulated first enclosure at a uniform temperature throughout an analysis. The at least one column module includes a computer processor, means for releasably securing the core unit to a column module, a capillary column, a capillary column heater member, and means for sensing and controlling the temperature of the capillary column. The capillary column has an analyte outlet member in fluid communication with at least one detector module. The at least one detector module has a computer processing unit, and an analogue to digital signal converter, means for releasably securing said core unit to the detector module. The detector module includes detector member within a thermally insulated enclosure.

15 Claims, 9 Drawing Sheets

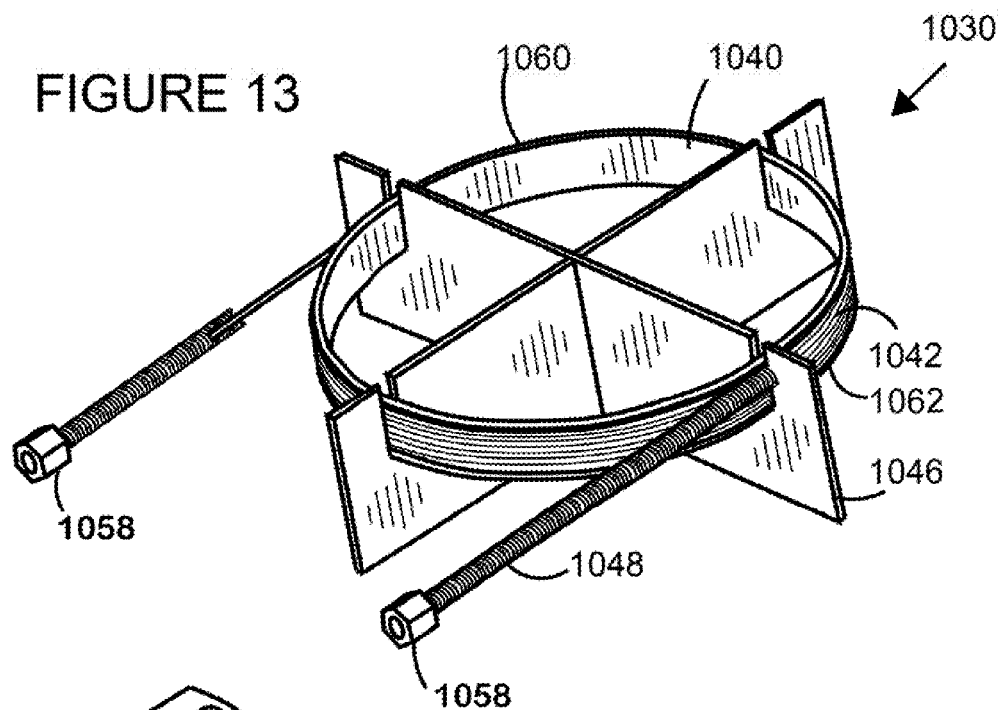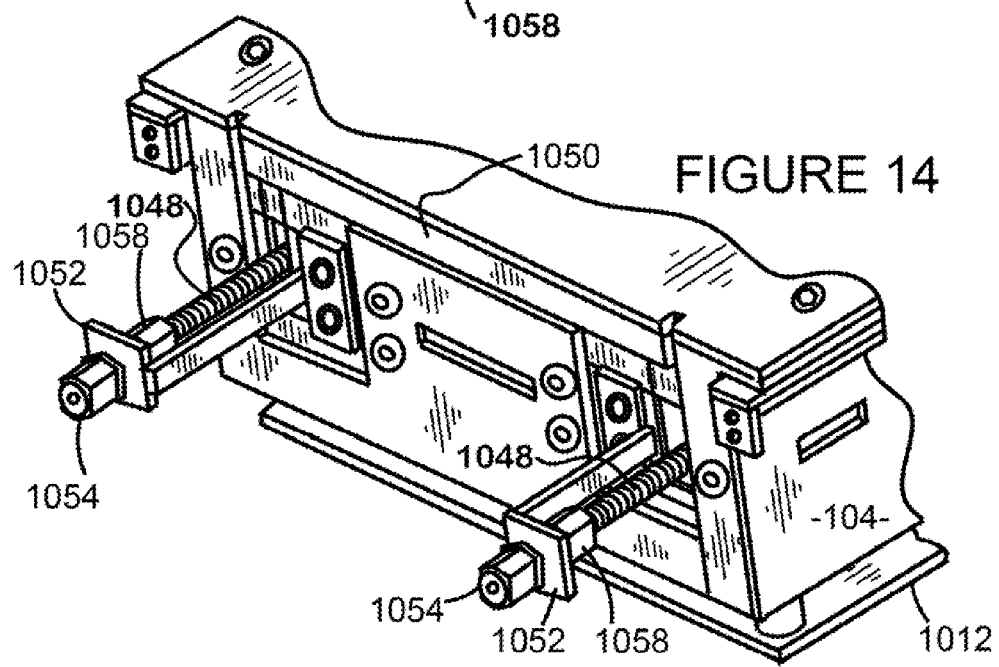

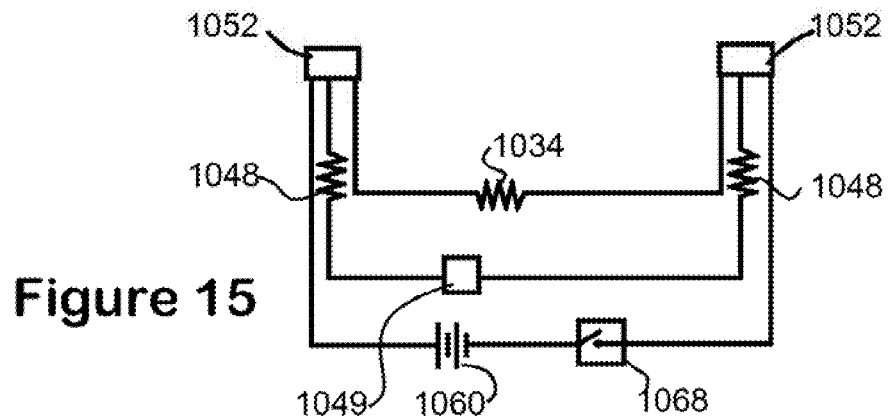
Figure 15
Figure 16
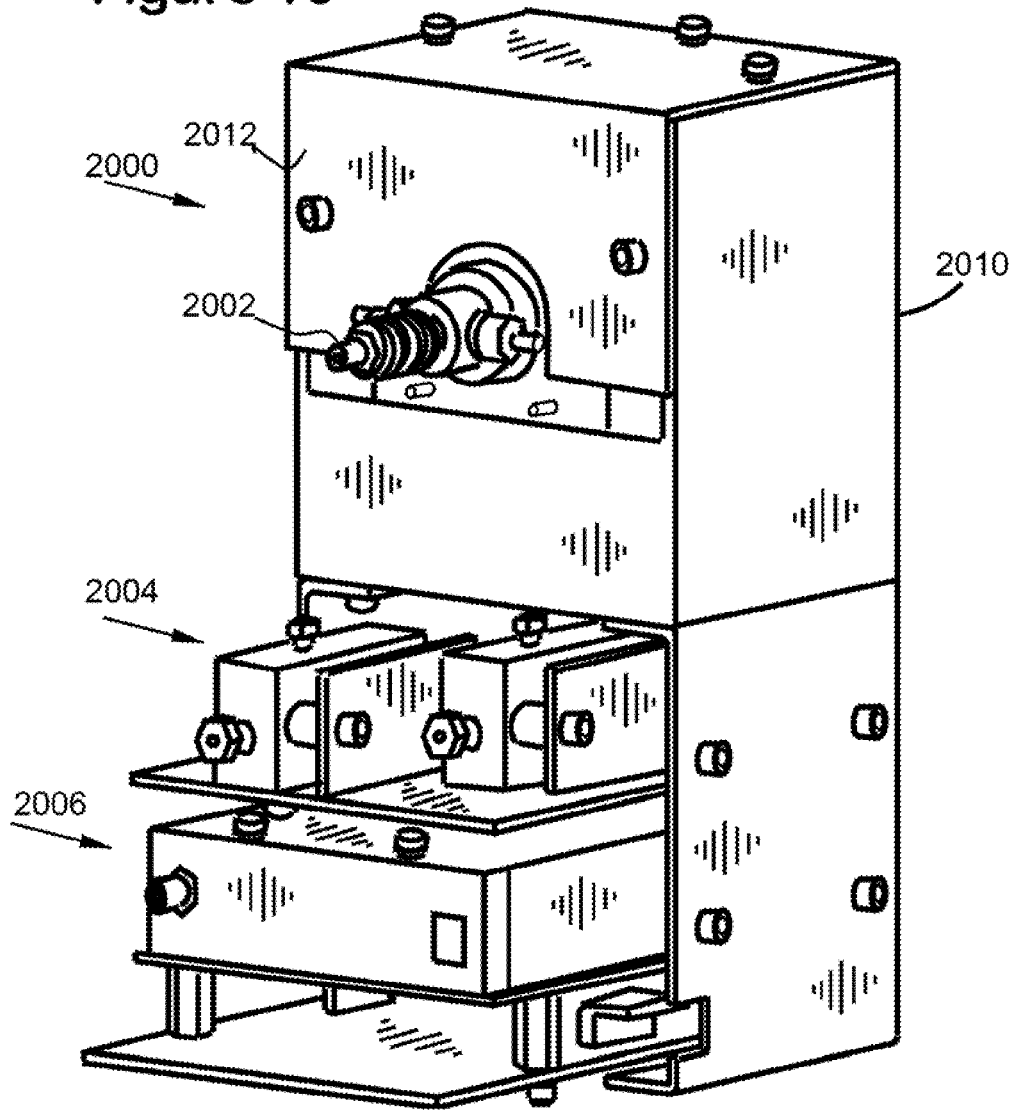

TRANS-CONFIGURABLE MODULAR CHROMATOGRAPHIC ASSEMBLY

CROSS-REFERENCE TO RELATED APPLICATION

This application is a continuation-in-part of pending patent application Ser. No. 12/555,783, filed Sep. 8, 2009, published as PCT/US2009/056281 on Mar. 11, 2010, and having the title, "Fast micro Gas Chromatograph System", the disclosure of which is incorporated by reference, as though recited in full.

FIELD OF THE INVENTION

The invention relates to a modular chromatograph system having a core unit, and at least one self-supporting column module and at least one self supporting detector module.

BACKGROUND OF THE INVENTION

Summary of the Invention

The present invention relates to a trans-configurable modular chromatograph. The term "trans-configurable", as employed herein, refers to a chromatograph that is composed of a plurality of self-supporting components. The configuration of the chromatograph can be changed by adding a component, or components, removing one or more components, or interchange one type of component for another type of component. Thus, the trans-configurable modular chromatograph is not merely assembled from a plurality of modular components, but can be reassembled to produce a new configuration.

In an embodiment of the invention, the chromatograph includes a core unit, at least one column module, and at least one detector module. The term "core unit" as employed herein, refers to the component of the chromatograph that is common to all configurations of the gas chromatograph modular system. The core unit is the substrate upon which a complete system is built. A complete system includes at least the core unit, one column module, and one detector module. It should be noted that a plurality of columns, detectors, or other equipment can be employed.

In accordance with the present invention, the chromatograph includes a core unit, and one column module, and one detector module, or a plurality of column modules and a plurality of detector modules, or one column module and a plurality of detector units, or a plurality of column modules and one detector module, etc.

In accordance with an embodiment of the invention, the core unit includes a controller module which includes a first computer processing unit, which has computer processor, computer memory, plurality of digital signal input/output ports, alpha-numeric character displaying member, and an analogue to digital signal converter. The core unit further includes a thermally insulated first enclosure. Within the thermally insulated first enclosure there is a first heater member, which is positioned to heat the interior of the thermally insulated first enclosure housing, and components within the enclosure. The components within the enclosure can include a heater, an injector, a first analytes stream inlet, a first analyte stream conduit, a stream switching mechanism, and a fan. Additionally, the core unit includes a temperature controller, which controls the heater member and is programmed to maintain the thermally insulated enclosure at a uniform temperature throughout an analysis.

In accordance with an embodiment of the invention a first column module includes a first computer processing unit having means for releasably securing the core unit to the first column module, capillary column, a capillary column heater member, a capillary column analyte inlet member, a capillary column analyte outlet member, and means for sensing and controlling the temperature of the capillary column. The capillary column analyte outlet member is in fluid communication with at least one detector module, and first computer processing unit includes a computer processor, computer memory, and a plurality of digital signal input/output ports.

In accordance with another embodiment of the invention a first detector module, includes a first computer processing unit, the first computer processing unit having means for releasably securing the core unit to the first detector module, a detector member, a detector member analyte inlet member, and a thermally insulated enclosure. The detector member is mounted within the thermally insulated enclosure, and the first computer processing unit includes a computer processor, computer memory, a plurality of digital signal input/output ports, and analogue to digital signal converter. The capillary column analyte outlet member is in fluid communication with the detector module inlet member.

In accordance with a further embodiment of the invention a plurality of the first detector module's first computer processing unit's plurality of digital signal input/output ports are in digital signal communication with a plurality of the core unit's first computer processing unit's plurality of digital signal input/output ports, and a plurality of the first column module's first computer processing unit's plurality of digital signal input/output ports are in digital signal communication with a plurality of the core unit controller module's plurality of digital signal input/output ports.

In accordance with another embodiment of the invention means is provided within the thermally insulated first enclosure for switching stream flow from the first analyte stream conduit to and between at least one column module and at least one detector module is a cross fluid connector. The means for switching stream flow from the first analyte stream conduit to and between at least one column module and at least one detector module can be an electromechanical or pneumato-mechanical switch, a Dean's switch, or any other switching mechanism as now or hereinafter known in the art.

In accordance with a further embodiment of the invention a trans-configurable modular chromatograph includes a core unit first heater member with a plurality of parallel radiation fins or holes and heating means for heating the plurality of parallel radiation fins or holes, and a fan member. The fan member is within the core unit thermally insulated first enclosure, and being positioned to distribute heat within the thermally insulated first enclosure housing. The heater serves to isothermally heat the first analytes stream inlet, the first analyte stream conduit and any other component that is within the thermally insulated first enclosure, such as a stream switching member and an injector.

In accordance with a still further embodiment of the trans-configurable modular chromatograph of the present invention, the core unit includes a core unit thermally insulated first enclosure which comprises an outer sheet metal enclosure, insulating means, and an inner sheet metal enclosure, and insulating means enclosed between the outer sheet metal enclosure and the inner sheet metal enclosure.

In accordance with a still further embodiment of the trans-configurable modular chromatograph of the present invention, the column module includes a capillary column that is spirally wound on a ring support. A thermal resistive member is substantially coextensive with the column, and the thermal resistive member and the column member are enclosed within a sheath member. A controller is provided for maintaining the thermal resistive member at a temperature equal to or above the maximum column operating temperature. The ring member is preferably aluminum or copper.

BRIEF DESCRIPTION OF THE DRAWINGS

The invention will be described in conjunction with the accompanying drawings, in which:

FIG. 13 is a perspective view of a cylindrical mounting ring and capillary column, including end heaters, including a fragmentary view of one of the end heaters, in accordance with the invention;

FIG. 14 is a fragmentary perspective view of a column module, in accordance with the invention;

FIG. 15 is a schematic illustration of wiring for a capillary column and the capillary column end heaters in accordance with the invention;

FIG. 16 is a perspective view of a detector module including pneumatic and electronic sub-modules in accordance with the invention;

DETAILED DESCRIPTION

It is advantageous to define several terms before describing the invention. It should be appreciated that the following definitions are used throughout this application.

Definitions

For the purposes of this disclosure, the term "analyte" shall refer to a substance or chemical constituent that is determined in an analytical procedure, such as a titration. An analyte (in analytical chemistry preferentially referred to as component) itself cannot be measured, but a measurable property of the analyte can.

For the purposes of this disclosure, the term "O.D" shall refer to outer diameter For the purposes of this disclosure, the term "I.D" shall refer to inner diameter For the purposes of this disclosure, the term "FID" shall refer to Flame Ionization Detector For the purposes of this disclosure, the term "FPD" shall refer to Flame Photometric Detector For the purposes of this disclosure, the term "TCD" shall refer to Thermal Conductivity Detector For the purposes of this disclosure, the term "SPU" shall refer to Sample Processing Unit For the purposes of this disclosure, the term "EPC" shall refer to Electronic Pressure Control For the purposes of this disclosure, the term "VSO" shall refer to Voltage Sensitive Orifice For the purposes of this disclosure, the term "RSD" shall refer to Relative Standard Deviation For the purposes of this disclosure, the term "RTD" shall refer to Resistance Temperature Device For the purposes of this disclosure, the term "VOC" shall refer to Volatile Organic Carbon For the purposes of this disclosure the term "core unit" refers to the assembly that is common to modifications of the gas chromatograph modular systems. It is the substrate upon which a complete system is built. A complete system includes at least the core unit, one column module, and one detector module. It should be noted that additional columns, detectors, or other equipment can be employed.

Self-Supporting Modular Components

The disclosed gas chromatograph ("GC") comprises at least three modules, each being electronically and mechanically, self-supporting. The primary module is a sample processing unit, and the secondary modules are one or more column modules and detector modules. The modular system provides for additional modules to be added as necessary or worn out modules replaced without rebuilding the entire system.

Figure 1:
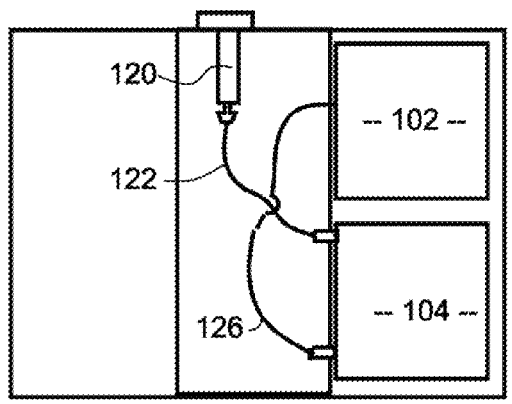
FIG. 1 is a plan view of a modular assembly having one self-supporting detector module and one self-supporting column module in accordance with the invention.

Examples of the versatility of the modular assembly 100 are illustrated in FIGS. 1-6. As will be illustrated, the modular assembly system 100 can contain one or a plurality of column modules. In a two column module system, for example, each module can have the same conductive capillary column type (e.g. two 180 µm ID, MXT-1 liquid phase coatings) or can be different (e.g. one 180 µm ID, MXT-1 liquid phase coating and one 320 µm ID, MXT-Alumina coating). This powerful use of two different conductive capillary column types in the same GC system, on the same injected sample, enable the shortcomings of the first column material to be met by the second and vice versa. For example, one column can be optimum for separation of one or more components from the feed stream while the other column can be optimum for separation of another component, or components from the feed stream. In FIG. 1 the assembly 100 contains a first detector module 102 and a first column module 104 which are in communication through conduit 126. An injector 120 is connected to the first column module 104 through conduit 122. In this configuration a single sample would be injected into column 104 and analyzed in detector 102.

Figure 2:
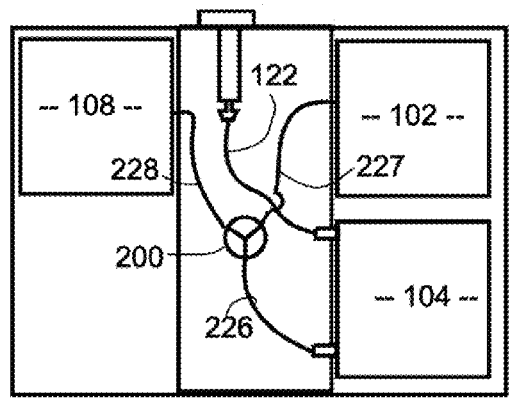
FIG. 2 is a plan view of a modular assembly having a first detector module, a column module and a second detector module in accordance with the invention.

In FIG. 2 a second detector module 108 has been added and is connected to the first column 104 through Y connector 200, and conduits 228 and 226. In this configuration the sample is injected directly through injector 120 into first column module 104. The first column module 104 is connected to the Y 200 through conduit 226 from which conduits 228 and 227 lead to second detector 108 and first detector 102 respectively. The use of dual detectors permits the identification of additional analytes. The flow into the two detectors can be sequential corresponding to different separation times of components coming through the capillary column 104.

Figure 3:
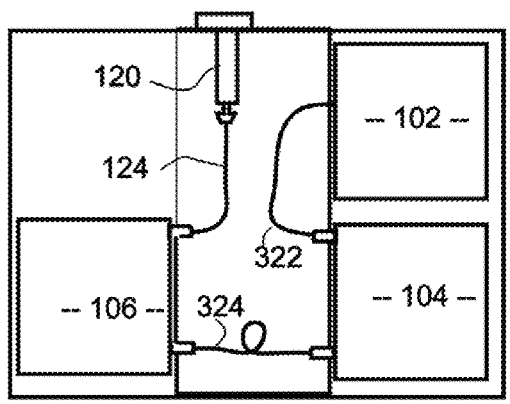
FIG. 3 is a plan view of a modular assembly having a first detector module, a first column module and a second column module in accordance with the invention.

In FIG. 3, the injector 120 is, through conduit 124, attached to a second column module 106 which is, through conduit 324, connected directly to the first column module 104. The analytes injected into the second column module 106 which then sends the analytes to the first column module 104 which are then sent to first detector module 102 through conduit 322. The dual column design enables higher degrees of separation in that one column is specific for the separation of first sub-groups of components and the other column is specific for the separation of the first sub-group into further sub-groups.

Figure 4:
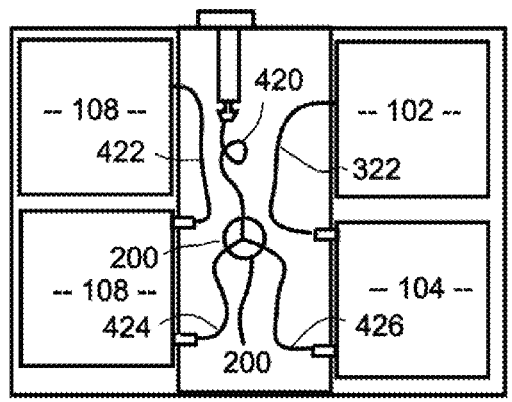
FIG. 4 is a plan view of a modular assembly having a first detector module, a first column module, a second detector module and a second column using a Y connector between the two columns, in accordance with the invention.

The combination in FIG. 4 illustrates the injector 120 connected to a Y connector 200 through conduit 420 and, through conduits 426 and 424 into first column module 104 and second column module 106 respectively. The first column module 104 is connected to first detector module 102 through conduit 322 and the second column module 106 to second detector module 108 through conduit 422. In this manner, there are two levels of component separation and individual detection for each of the two levels of separation.

Figure 5:
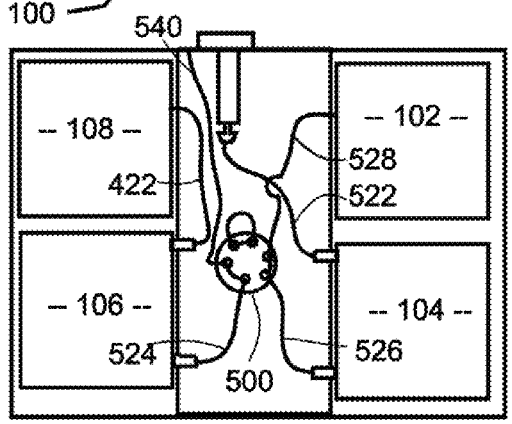
FIG. 5 is a plan view of a modular assembly having a first detector module, a first column module, a second detector module and a second column using a switching valve between the two columns, in accordance with the invention.

In FIG. 5 the first column module 104 and second column module 106 are used along with first detector 102 and second detector 108, as illustrated in FIG. 4. In this figure, a switch 500 is used to add the ability to control the path of the analytes. The injector 120 is connected directly to the first column module 104 through conduit 522. From the first column module 104 the analytes enter the switch 500 through conduit 526. From the switch 500 the analytes can be directed through conduit 524 to column module 106 or to first detector 102 through conduit 528. From second column module 106, the analyte passes through conduit 422 to second detector 108. In this embodiment conduit 540 is illustrated to feed an auxiliary carrier gas into the switch 500.

Figure 6:
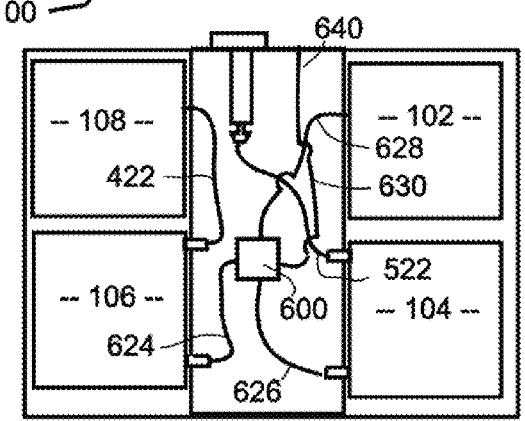
FIG. 6 is a plan view of a modular assembly having a first detector module, a first column module, a second detector module and a second column using a Dean's switch between the two columns, in accordance with the invention.

In FIG. 6 the arrangement is the same as in FIG. 5 with the exception of a Dean's switch 600 being used. Therefore, the injector 120 injects the analyte into first column module 104 through conduit 522 where it enters the Dean's switch 600 through conduit 626. From the Dean's switch 600 the analyte can enter either second column 106 through conduit 624 or first detector 102 through conduit 628. Analyte entering second column module 106 exits to second detector 108 through conduit 422. The auxiliary carrier gas conduit 640 feeds into the Dean's switch 600 for dispersal as described above.

The embodiments of FIGS. 5 and 6 are designed for use when two or more analytes have the same separation time through first column module 104. For example a first analyte exits first column module 104 and is directed into first detector module 102. Switch 500 or 600 is activated to send two or more analytes having the same separation time through the first column module to a second column module 106 for further separation and then to the second detector 108. Switch 500 or 600 can then be deactivated to direct other analytes from first column module 104 to first detector module 102. This heart cut technique is only one of a suite of techniques known as column switching to those skilled in the arts. Simple valve and plumbing implementations within the isothermal oven 803 enable back flush, bypass, trap/bypass, etc.

It should be noted that although only one detector module and one column module will be referred to hereinafter, this is not to limit the scope of the invention but rather to make the description more readable.

Sample Processing Unit

Figure 7:
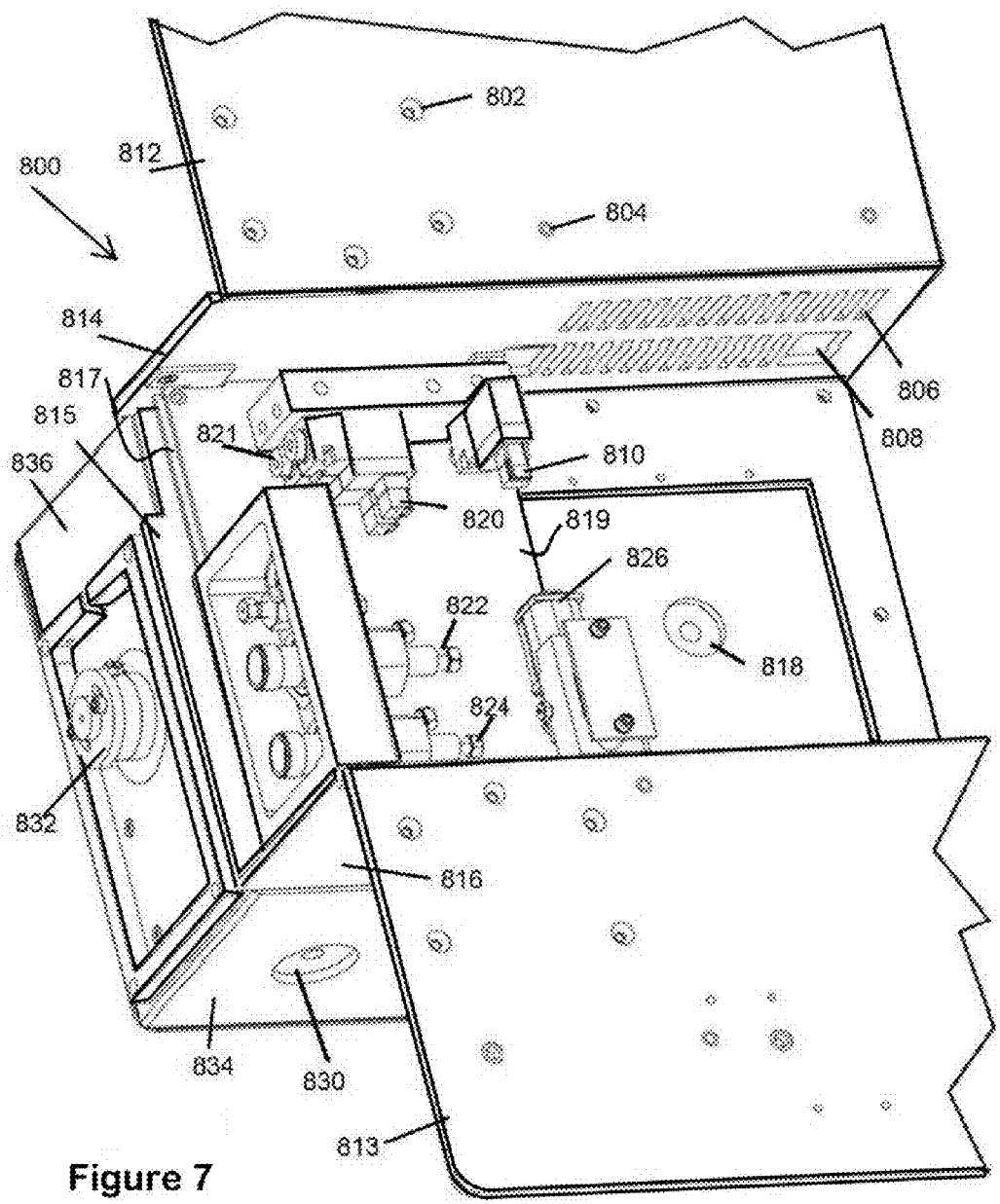
FIG. 7 is a perspective view of the electronics area of the core unit in accordance with the present invention.

The modular components are physically arranged around the centrally located Sample Processing Unit (SPU) 800 as illustrated in FIG. 7, and which serves as the core unit for the modular assemblies as illustrated in FIGS. 1-6. The SPU 800 contains an isothermal oven compartment as best viewed in FIGS. 7 and 8, which houses the injection port inlet 832, injection port 120, cross stream splitter 914 fan 902, heater radiation fins 908, and thermal insulation 904. The interior components are housed within a sheet metal frame 906. An electro-pneumatic compartment 801, as best seen in FIG. 7, contains electronic pressure controllers/flow controllers 826, on/off solenoid valves 810, 820, 821, septum purge needle valve 822, and split-vent needle valve 824, as well as any additional optional equipment, needed for proper pneumatic functioning of the GC system 100, the SPU circuit board 817 which controls the aforementioned components, as well as the SPU heater circuits.

The components are enclosed within a chassis, preferably formed of single sheet of metal, having sides 812, 814, 815, 816 and 813 that are bent to form wings 812 and 813 that are provide with detector mounting holes 802 and the PCB mounting stud 804. The pneumatics mounting plate 819 serves as a mount board. Construction of the chassis will be known to those skilled in the arts. To prevent overheating of the components, air circulation vents 806 are provided in both of the sides 814 and 816. Adjacent to the air circulation vents 806 is the wire harness through hole 808. Although placed adjacent the air circulation vents 806, the wire harness through hole 808 can be place along one of the sides 814, 816 at any place convenient for the interior arrangement. In the bottom portion of the SPU 800 is a thermal insulation through hole 818.

Figure 8:
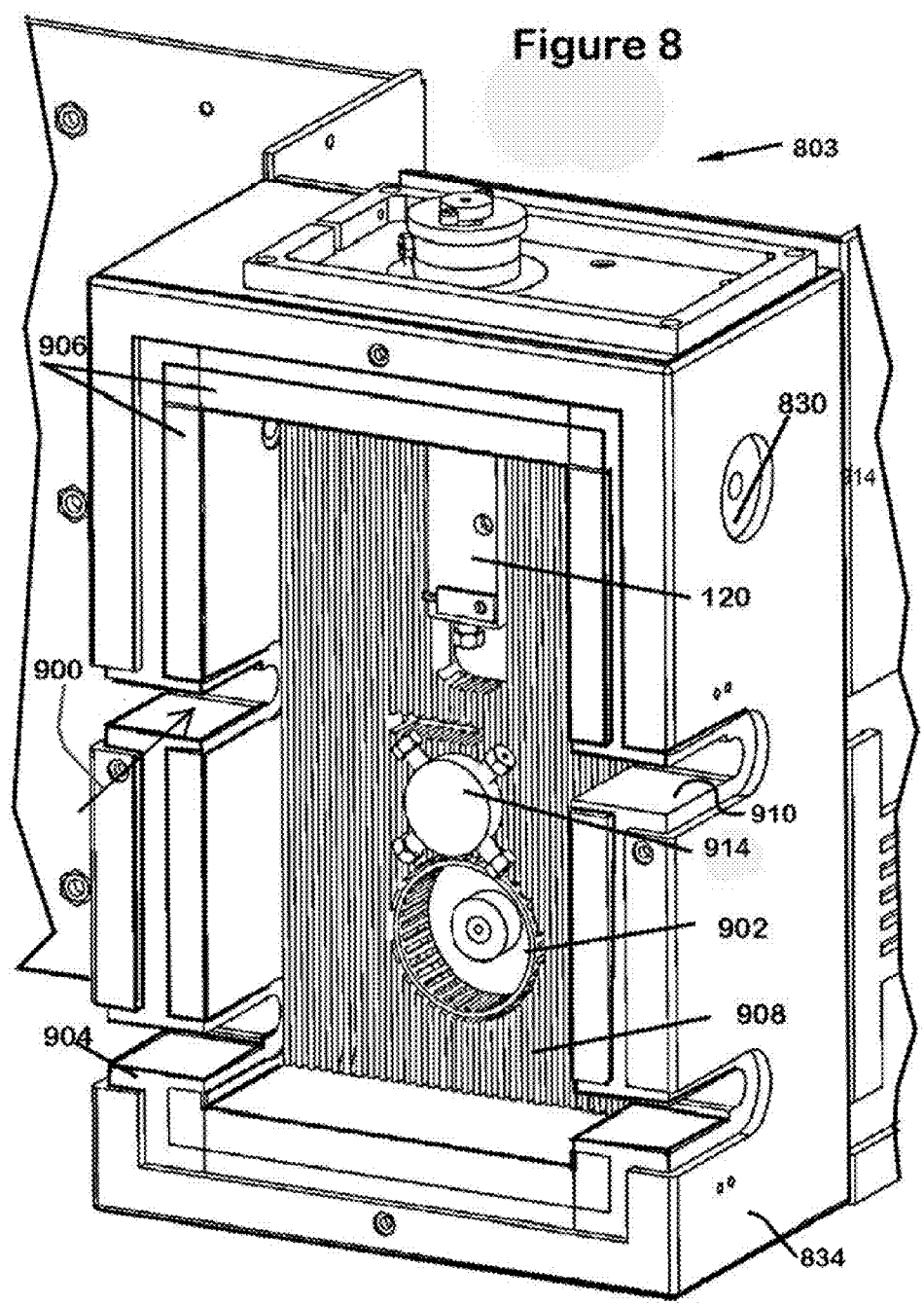
FIG. 8 is a perspective view of the core unit illustrating the isothermal oven, heating element, fan, cross stream splitter, and injector, in accordance with the invention.

Adjacent to the electro-pneumatic compartment 801 is the heating compartment 803, the interior of which is shown in FIG. 8, which operates as an isothermal oven. The heating compartment has insulated sides 834 and 836 and a cover (not shown). Housed within the isothermal oven 803 are components that must be maintained at a constant, precise, elevated temperature relative to ambient. The SPU isothermal oven 803 preferably contains a finned or other high surface area heat sink 908, to which a heater is attached. The SPU isothermal oven 803 can also contain a mixing fan 902 for distributing heat evenly throughout the oven as well as a switching mechanism such as switch 500 or 600, splitter or cross stream splitter 910, as shown in FIG. 8 and described heretofore in FIGS. 5 and 6. Passages are provided for the end heater components described in detail hereinafter. The end heaters are inserted in the direction indicated by arrow 900.

The SPU isothermal oven 803 contains the sample injection port 120 that has an internal glass liner used for sample introduction in either a user selectable split or splitless mode. The injection port 120 also contains a recess where a replaceable sealing septum resides. A metal cap holds the septum in place and provides an opening whereby a needle can be inserted for the purpose of injecting sample into the inner space of the injector glass liner.

The isothermal oven 803 is lined with insulation 904 between the interior wall 906 and exterior walls 834, 834, top 836 and bottom (not shown). In this illustration the cross stream splitter 914 is shown, however any splitter or switching valves used, whether or not illustrated herein, would be located within the isothermal oven 803.

The SPU isothermal oven 803 can contain transfer and/or flow restricting tubes of various lengths and inside diameters which are in fluid communication with the injection port 120, Column Modules 104 and 106, Detector Modules 102 and 108 and stream splitting/switching devices. Tubes directly attached to Column Module inlet and outlet connectors are preferably non-conductive in order to electrically isolate the charged Column Module end connectors from the rest of the system.

Figure 9:
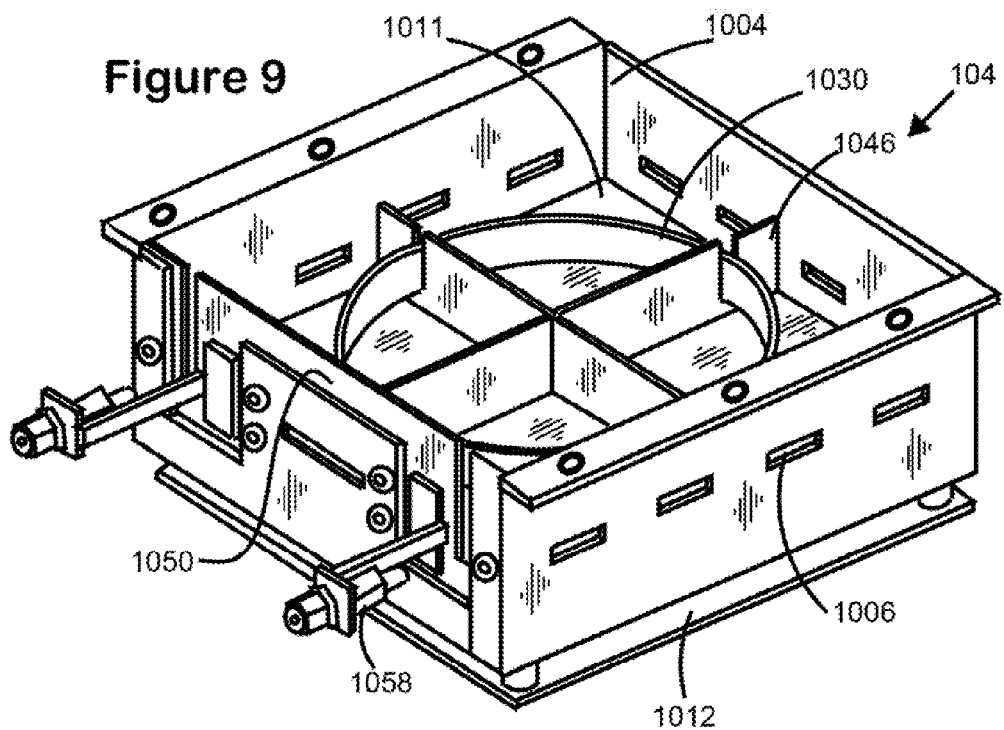
FIG. 9 is a perspective view of the interior of the column module, without the column, in accordance with the invention.

The isothermal oven 803 and associated thermal insulation preferably contain slots 910, for enabling column modules 104 and 106, as seen in FIGS. 9, 13, and 14 to be inserted and removed from the GC system 100 with only one axis of movement as indicated by arrow 900, after mounting hardware and the insulated lid are removed. The column module heated ends 1048 pass through the passageways as illustrated by arrow 900, in FIG. 8. The passageways 910 are closed with insulation when the column module 104 and/or 106 is in place, in order to maintain the column ends in an isothermal environment.

Figure 17:
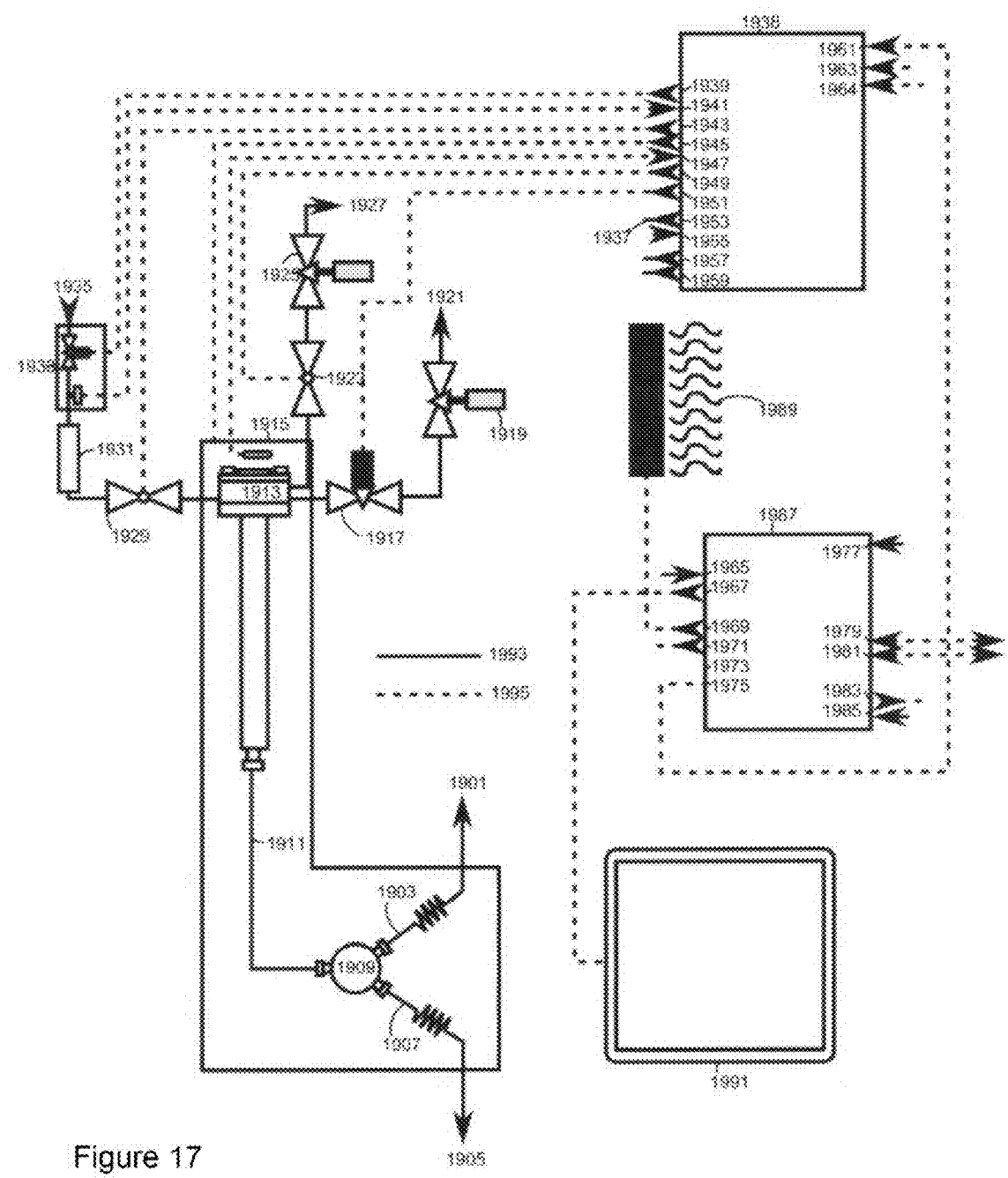
FIG. 17 is a schematic illustration of wiring and plumbing lines for a core unit in accordance with the invention.

Flow Restrictors 1903 and 1907, as seen in FIG. 17 are installed between the low volume splitter tee 1909 and the two columns in order to increase the system operating pressure above what would normally be needed to drive the correct linear velocity of the carrier gas through the short columns that are used. These restrictors are generally 50 um I.D. deactivated fused silica and are necessary for columns greater than 100 um in I.D. The relative restriction values of both restrictors (i.e. their lengths) must be exactly the same if flow rates through the two different columns are to be equal.

The separation column 104 is housed in a self-contained module which includes all of the electrical controls and hardware necessary for rapid temperature programming through the use of resistively heated metal capillary column material and cooling independent of the other modules in the instrument. The material can range in size from 100 um I.D. to 320 µm I.D.

Figure 12:
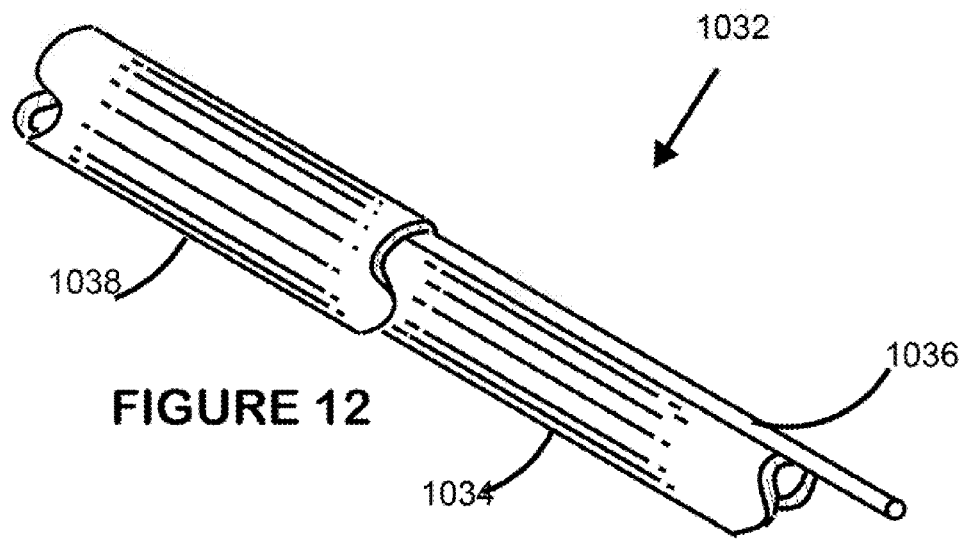
FIG. 12 is a perspective view of a capillary column, including an RTD wire, and a sheath enclosing the capillary column and the RTD wire.

Sample components introduced into the GC modular assembly 100 at the injection port 120 are transferred to uniquely designed "smart" column modules 104, as shown in FIG. 9, for separation. At the heart of the column module 104 is a conductive capillary chromatography separation column 1034, as shown in FIG. 12, which performs the physical separation of chemical components as they traverse its length and interact with the special coating on the inside of the capillary tube.

Several different types of conductive capillary columns exist and are well known in the art and the disclosed modular system 100 system can easily contain any of these conductive capillary column types. Typical variations include different internal coating types (e.g. liquid coatings and porous layer coatings), coating thicknesses, as well as different inside diameters (ID) of the conductive capillary tube up to and including 320 micrometer (µm) ID. Each conductive capillary column type has its own advantages as well as shortcomings depending on the chemical compounds one wishes to separate. Common suppliers include Restek's MXT metal capillary column material, Agilent's Prosteel metal capillary column material, Quadrex's Ultra-Alloy metal capillary column material, as well as, VICI Valco's nickel coated fused silica capillary column material. Aluminum clad fused silica capillary columns could be employed in a Column Module, but are generally avoided due to the thermal stress fractures that develop in the aluminum cladding during repeated temperature cycling.

Figure 11:
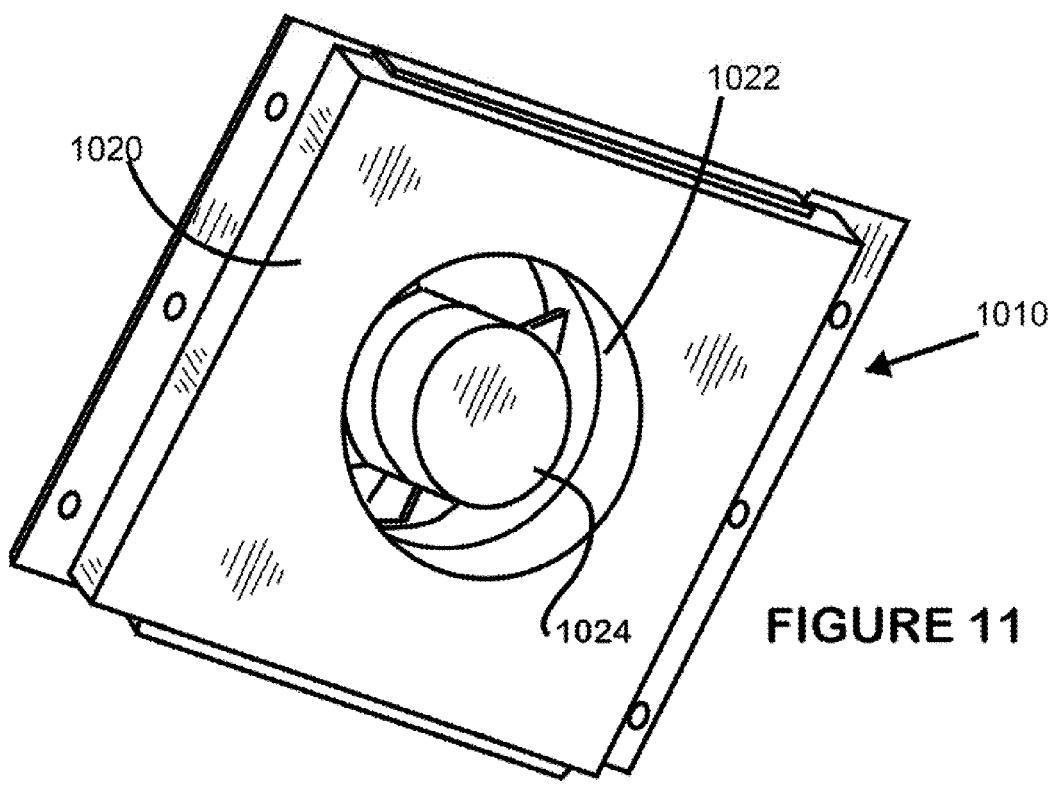
FIG. 11 is a perspective view of a lid and fan of a column module, in accordance with the invention.

Column modules 104 and 106 consist of a small enclosure 1004 with a lid 1010, as shown in FIGS. 9 and 11. The lid 1010 and bottom 1011 contain layers of high temperature thermal insulation, preferably polyimide foam to retain the desired temperatures. A column coil support 1046 maintains the column coil assembly 1030 in position, as shown in detail in FIG. 9, and a column end connector attachment plate 1050.

The column coil support 1046 is a low thermal conductivity material, preferably mica, or a fiberglass printed circuit board. Electrical contacts (not shown) are provided for the connection of resistance heater wire.

Figure 10:
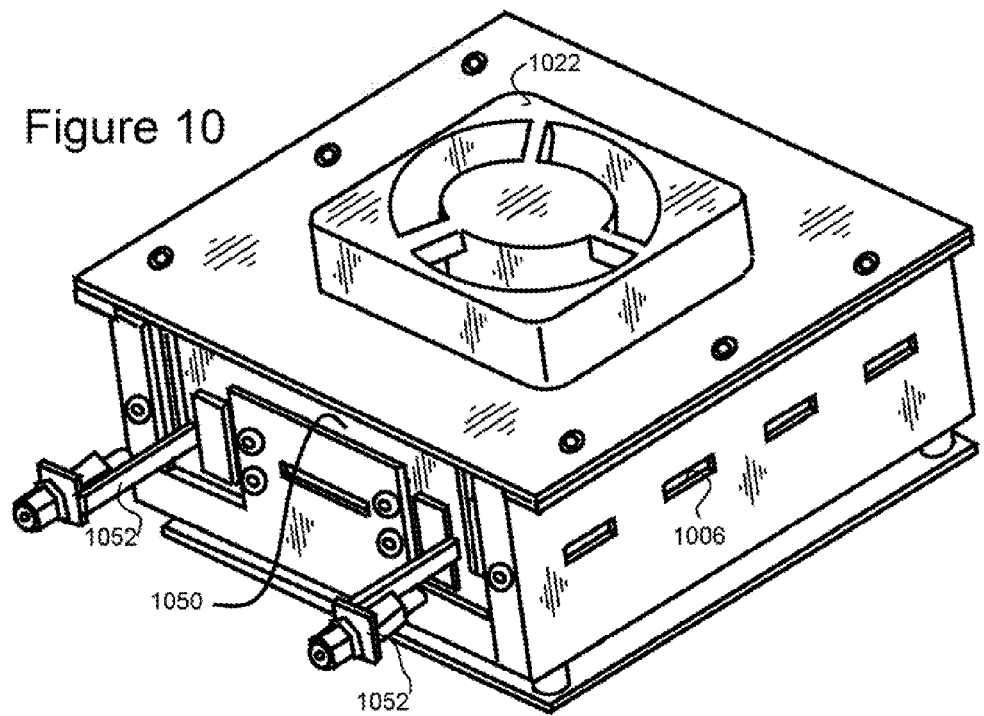
FIG. 10 is a perspective view of a column module with lid and fan, in accordance with the invention.

Attached to the top of the Column Module 104 is a lid 1010 with a centrally located exhaust hole 1022, as illustrated in FIGS. 10 and 11. Thermal insulation 1020 is affixed to the inside surface of the lid 1010 and a small box fan 1024 is attached to the exterior surface over the exhaust hole 1022. The box fan 1024 draws cool air in from perforations 1006 located around the periphery of the main column module 104 enclosure and through the exhaust hole 1022 located on the lid 1010. This serves the purpose of rapidly cooling the column coil assembly 1030 of FIG. 13 after a programmed temperature chromatographic analysis is performed. The end regions of the column 1032 are heated by coiled resistance heating wire 1048, (FIG. 13).

Attached to the bottom of the column module 104 on standoffs is a printed circuit board (PCB) 1012 containing a microprocessor. The column module 104 PCB 1012 electronic components serve to independently control the column module 104's electronic functionality. This includes but is not limited to storing programmed temperature cycle parameters, calibration parameters, column module identification information, maximum temperature limits, and cycle counters. This also includes the feedback temperature control of the column coil assembly 1030, control of the power to the column end heaters and on/off control of the cooling box fan 1024. The column module PCB 1012 also communicates directly with the SPU PCB.

The column coil assembly 1030, as shown in FIG. 13, contains a capillary bundle 1032 illustrated in detail in FIG. 12, made from an electrically conductive open tubular capillary chromatography column 1034, and a RTD wire 1036 coated with a thin, high temperature insulating layer, preferably polyimide, arranged nominally in parallel and in intimate thermal contact with the capillary chromatography column 1034. An insulating high temperature sheath 1038, preferably made of fiberglass, tightly encases the capillary chromatography column 1032 and RTD wire 1034 into a single linear column bundle 1032.

In order for rapid temperature programming to be possible, some form of temperature sensing must be incorporated very near to the metal column material that is being resistively heated. This is accomplished by inserting both the capillary chromatograph column 1034 and a very small diameter wire (~0.002" dia.) coated with electrically insulating, high temperature polyimide resin 1036 co-linearly into a high-temperature fiberglass sheath 1038. The small diameter wire 1036 is then fitted with low resistance lead wires and used as a RTD device 1036 for the feedback control loop that provides the temperature modulation. Due to the intimate contact between the RTD wire 1036 and the capillary chromatograph column 1034 and the low mass of each, the thermal transport delay between the two is very small which results in a very fast, accurate control loop.

This results in the elimination of temperature gradients along the length of the capillary column bundle 1032 and consequently the ability to obtain maximum separating efficiency from the capillary column material. Also a part of the column coil assembly 1030 is a thin, conductive metal cylinder 1040 with externally raised edges onto which the linear column bundle 1032 containing the capillary column 1034 and RTD wire 1036 are wrapped in tight cylindrical coils 1042, as shown in FIG. 14, holding the column bundle 1032 in a very uniform, compact geometry. The raised upper lip 1060 and lower lip 1062 keep the capillary bundle from slipping off the ring 1040. The compact, cylindrical coils 1042 of the column coil bundle 1032 also aid in conserving heat during heating cycles due to adjacent coils 1042 being in thermal communication with one another, but simultaneously allow for rapid cooling of the coil assembly 1032 due to its narrow cross section. Electrical shorts between adjacent coils of the capillary bundle 1032 and the aluminum cylinder 1040 are avoided due to the high-temperature fiberglass sheath 1038 that covers the column material and sensor wire 1036. The metal ring 1040 is preferably made of relatively low mass aluminum, but other high thermal conductivity metals can be used, such as copper and brass.

There are two factors that limit the maximum length of material that can be installed in a column module 104. The first is the number of coils that can be physical wrapped compactly around the conductive metal ring 1040 in the space reserved for the column module 104 in the instrument design. The second is the maximum heating rate that is desired for a given length of column material. This is due to the relatively high resistance of the metal column material and Ohm's law. The basic trade-off reduces to longer columns having to be heated at lower maximum rates than shorter columns, simply because the amount of power that can be dissipated in the metal tube falls off linearly with increasing length. However, as column length increases slower heating rates become necessary to extract the maximum resolution from the column, so the trade-off is somewhat balanced.

An example ring tested on the prototype was approximately 3" in diameter with a wall thickness of 0.025". The high thermal conductivity of aluminum serves a very important function for the overall efficient heating of the column material by dissipating thermal "hot-spots" generated during heating thereby creating a more uniform temperature distribution along the length of the column material. The more uniform the temperature distribution is the more efficient are the resulting component separations.

Also a part of the column coil assembly 1030 are lengths of small, dense coils of heater wire 1048 that encircle the free ends of the column bundle 1032 which exit tangentially from the coil ring 1040. These small heater coils 1048 comprise the column end heaters and are used to eliminate cold spots by providing supplemental heat to the free ends of the column coil bundle 1032. The overall diameter of the small coils 1048 is nominally 1/8" with the wire diameter being nominally 0.010" and preferably made of a nickel-chromium alloy. The ends of the small coils 1048 are attached such that the individual adjacent coils of wire are expanded and slightly separated from one another preventing a short circuit from one coil to the next.

The column coil support member 1046 resides within the column module 104 enclosure and is comprised of two slotted sheets of material that is both thermally and electrically insulating and is preferably rigid mica sheet or printed circuit board sheet. The sheets are orthogonally interleaved to form a cross into which the column coil assembly 1030 rests. Where a printed circuit board is used, electrical lines can have junction points on the circuit board.

Each free end of the column coil bundle 1032 is joined both electrically and pneumatically to a separate column end connector 1052 that consists of an elongated "Z" shaped metal bracket with the end farthest from the column module 104 enclosure having a small pneumatic metal fitting 1054 attached, as shown in FIG. 14. The column end connectors 1052 are attached to the column end connector attachment plate 1050 which in turn is attached to one side of the column module enclosure 104. The column end connector attachment plate 1050 is made from an insulating sheet, preferably rigid mica sheet or printed circuit board sheet, and serves to electrically isolate the conductive column material while providing extended mechanical support structures for the column coil bundle 1032 ends. The column end connectors 1052 are extended away from the column module 104 enclosure in order for them to protrude into the SPU isothermal oven of FIG. 8, thereby eliminating them as potential cold spots in the analytical flow path.

The capillary column ends are attached to the pneumatic metal fittings 1054, with conductive metal ferrules (not shown). The metal ferrules both seal the column ends to the metal fittings 1054 pneumatically as well as provide electrical continuity between the conductive capillary bundle 1032 and the column end connectors 1052. This enables the column end connectors 1052 to be used as electrical nodes for attaching lead wires from the column module PCB 1012. Power is applied to these nodes to resistively heat the conductive capillary column 1034 and simultaneously the column end heaters 1048.

The column end heaters 1048 attach to the column end connectors 1052 through the use of a specially designed column nut 1058, which contains a threaded stud on one end. The small column end heater wire 1048 is threaded onto the column nut 1058 stud creating a mechanical and electrical connection to the column end connector 1052 node. The opposite ends of the column end heater wires 1048 are attached to the column coil support 1046 immediately adjacent to the point where the column bundle 1032 leaves the column coil cylinder 1040. Lead wires attach to each column end heater wire 1048 at this point and plug into the column module PCB 1012 at their opposite ends.

With the sheathed column material 1034 tightly and compactly coiled on the aluminum support ring 1040, a large reduction of surface area is created along the entire length of the column 1034. This reduces convective heat losses and consequently the power required to heat the column 1034 at a given linear temperature ramp. However, the free ends of the sheathed column assembly 1030 that are not wrapped on the aluminum support ring 1040 have a much larger surface area per unit length of column material exposed to free convection that results in a lower temperature profile relative to the coiled main body of the column material. This differential temperature profile between the free ends and the main body is only exacerbated as the column main body temperature increases and can result in poor chromatography at column temperatures above ~200 deg. C.

To alleviate this problem without implementing a separate actively controlled heater circuit to provide extra heat to the free ends, a heater circuit 1048 as show in FIG. 15 was created that connects in parallel with the main heater circuit 1060. The heaters 1048 can consist of pre-wound NiChrom wire coils purchased in bulk and then cut to the needed length. One end of the coil is attached to the end connector threaded nut while the other end connects to the insulating column support structure. The free ends of the column pass through the center of the heater coils 1048 thereby providing them with consistent, even heat along their entire length.

The heater coil 1048 ends that attach to the column support structure are connected to the column module PCB 1012. As shown in FIG. 15, the PCB 1012 contains a transistor 1049 which, when activated, connects both end heaters 1048 together in series. Pulsing the transistor 1049, or alternatively pulsing a switch 1068, provides a means to control the current passing through each end heater and consequently the power dissipated in each.

Since the temperature of the coiled main column assembly 1042 body is actively controlled and the end heater coils 1048 are operated passively in parallel, the power dissipated in the end heater coils 1048 is proportional to the power dissipated in the main column assembly 1042 body based on the total series resistance of the end heater circuit.

The conductive capillary chromatograph column 1034 is thermally modulated through resistive heating by applying power directly to the column end connectors 1052. The voltage applied to the column end connectors 1052 is precisely regulated by a PID negative feedback control loop implemented in the column module PCB 1012. Due to the low thermal mass of the conductive capillary column 1034 and RTD sensor wire 1036, as well as their intimate contact with one another, very accurate, fast linear temperature program ramps of the conductive capillary column are attainable from 0.05 deg. C/sec to 10 deg. C/sec.

Detector Modules

Detector modules 102 consist of independent, compact, self-contained subsystems that work in conjunction with the SPU 1012 and column modules 104 to perform a complete chromatographic analysis. Its ultimate function is to obtain intensity versus time characterization of the sample stream exiting the column module 104, 106 as it relates to the amount of mass per unit time or concentration of sample molecules that exist in the capillary column's mobile phase or carrier gas.

The detector module 102 contains all electronics and hardware necessary to convert a chemical signal from the effluent of a capillary separation column into a time-based digitized electrical signal where signal magnitude is proportional to chemical concentration. The electronics are capable of controlling heaters for isothermal ovens, pressure controllers or flow controllers for supply gases (e.g. hydrogen and air for a flame ionization detector), and signal transducer circuitry for converting an analyte molecular concentration or mass rate analogue data stream into a digitized data stream that can be recorded and ultimately used to quantify and/or identify chemical components.

An example detector module 2000, as shown in FIG. 16, is constructed on a compact structural framework or chassis 2010 that can be internally compartmentalized with each compartment having sub-modules that attach to the chassis 2010 and fulfill a different functional requirement for the detector module 2000 as a whole. Each compartment sub-module can be easily inserted or removed from the main detector module 2000 chassis which greatly simplifies manufacturing assembly and part replacement in the field.

In this example of a complete detector module 2000, flame ionization Detector Module 2000 can have a top level isothermal oven 2012 compartment containing the flame ionization mechanical components 2002 which must remain at a stable, elevated temperature relative to ambient for normal operation. Attached below the isothermal oven 2012 resides a pneumatic sub-module 2004 which contains electronic pressure or flow controllers supplying precise flows of hydrogen and air through small tubing to the above flame ionization mechanicals. Attached directly below the pneumatic sub-module 2004 sits the electronics sub-module 2006 that consists of a main microprocessor based PCB and an electrometer PCB. The main PCB controls the hydrogen and air pressure/flow controllers, the isothermal oven, the flame ionization ignition source and the electrometer auto-zero function. It also digitizes and conditions the signal received directly from the adjacent electrometer as well as communicates with the GC system communication PCB 1012.

Several different types of chromatographic detectors exist and are well known in the art. Each detector type has its own advantages as well as shortcomings. Some of these detectors include flame ionization detectors (FID), thermal conductivity detectors (TCD), flame photometric detectors (FPD), electron capture detectors (ECD), pulsed discharge detectors (PDD), argon ionization detectors (AID), photo-ionization detectors (PID), plasma emission detectors, and various mass spectrometry detectors (MSD). Detector Modules in the GC system can contain any of these detector types provided that the mechanical and electrical components of the detector can be made to fit appropriately in the space available for the module.

As stated heretofore, the GC systems as described above can contain one or two detector modules. In a two detector module system, each module can be of the same type (e.g. two FID detectors) or can be different (e.g. one FID and one TCD). Again, this powerful use of two different detector types allows the shortcomings of the first detector to be met by the second and vice versa. With the ability to couple different detector types with different column types in the same GC system, the number and type of chemical compounds that can be separated and quantified in a single analysis is greatly expanded.

Figure 18:
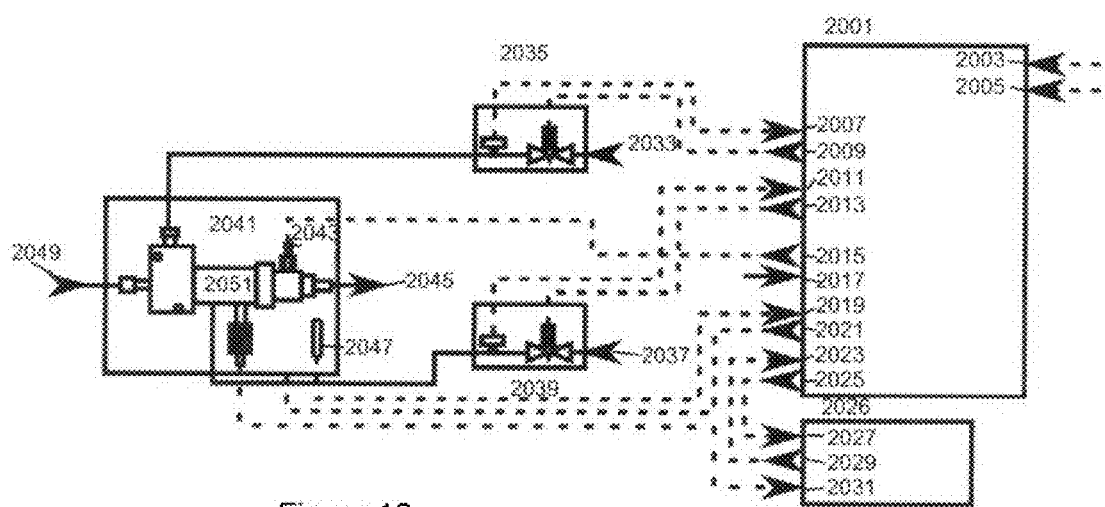
FIG. 18 is a schematic illustration of wiring and plumbing lines for a detector module in accordance with the invention.

Some instrument configurations can contain two Detector Modules with different types of detectors (e.g. FID and FPD or FID and TCD) for a single Column Module where the effluent from the column is split between the two for simultaneous analysis. Example schematics are illustrated in FIGS. 17 and 18, however other connections, both electrical and physical, will be known to those skilled in the art.

The column module 1901 is connected by a tube 1993 through flow restrictor 1 1903 to split Y 1909. A second column module 1905 is connected by a tube 1993 through flow restrictor 2 1907 to split Y 1909. The split Y 1909 is connected by tube 1993 through the heated zone 1911 to the inlet 1913.

The inlet 1913 is connected by tube 1993 to the N.O. valve column head pressure 1929 which is then connected to the ballast volume 1931, which is then connected to the EPC 1933, which is then connected to the carrier gas 1935. The inlet 1913 is also connected to the split vent proportional valve 1917 which is then connected to the split vent needle valve 1919 which then goes to the vent 1921. The inlet 1913 is also connected the N.O. valve septum purge 1923 which is connected to the septum purge needle valve 1925 which then goes to the vent 1927.

The SPU PCB 1938 has a 12 V output proportional valve 1939 that is connected by wire 1995 to the EPC 1933. The SPU PCB 1938 has an input pressure sensor (H2) 1941 that is connected to the EPC by wire 1995. The SPU PCB 1938 has a 12 V output on/off 1943 connected to the N.O. valve column head pressure 1929 by wire 1995. The SPU PCB 1938 has an output 24 V resistance heater 1945 that is connected to headed zone 1911. The SPU PCB 1938 has an input RTD 1947 that is connected to RTD 1915 by wire 1995. The SPU PCB 1938 has a 12 V output on/off 1949 connected to N.O. valve septum purge 1923 by wire 1995. The SPU PCB 1938 has a 12 V output proportional valve (split vent valve) 1951 connected to the split vent proportional valve 1917 by wire 1995. The SPU PCB 1938 has a 24 V output resistance heater connected to the spare heater 1937. The SPU PCB 1938 has an input RTD 1955 connected to the spare heater 1937. The SPU PCB 1938 has a 12 V output on/off 1957 and a 12 V output on/off (multi-event) device 1959.

The communication PCB 1987 has an input contact closure in 1965. The communication PCB 1987 has an output display bus 1967 connected to the display 1991. The communication PCB 1987 has an output 12 V on/off 1969 that connects to the cooling fan (case) 1989. The communication PCB 1987 has a 12 V output on/off spare 1971. The communication PCB 1987 has an RS-485 (Det. Bus). The communication PCB 1987 has an RS-485 (main bus) connected to the SPU PCB 1938 RS-485 1961, 24 V DC 1963 and 12 V DC 1964. The communication PCB 1987 has a 12 V DC input 1977. The communication PCB 1987 has an input/output RS-232 1979. The communication PCB 1987 has an input/output Ethernet 1981. The communication PCB 1987 has an output autosampler start 1983. The communication PCB 1987 has an input contact closure in 1985.

What is claimed is:

1. A trans-configurable modular chromatograph comprising:
   a—core unit,
      said core unit having,
         controller module, said controller module having,
            first computer processing unit, said first computer processing unit having,
               computer processor,
               computer memory,
               plurality of digital signal input/output ports,
            alpha-numeric character displaying member, and
            analogue to digital signal converter,
            thermally insulated first enclosure, said thermally insulated first enclosure having
            first heater member,
               said first heater member being positioned to heat said thermally insulated first enclosure housing, said first analytes stream inlet, and said first analyte stream conduit,
            a temperature controller,
            first analyte stream inlet,
            first analyte stream conduit in fluid communication with said analyte stream inlet,
               said temperature controller controlling said first heater member and programmed to maintain said thermally insulated first enclosure at a uniform temperature throughout an analysis;
   b—first column module, said first column unit having
      first computer processing unit,
      said first computer processing unit having;
         computer processor,
         computer memory,
         plurality of digital signal input/output ports,
         means for releasably securing said core unit to said first column module,
         capillary column,
         capillary column heater member,
         capillary column analyte inlet member,
         capillary column analyte outlet member,
            said capillary column analyte outlet member being in fluid communication with at least one detector module,
         means for sensing and controlling the temperature of said capillary column; and
   c—first detector module, said first detector module having
      first computer processing unit,
         said first computer processing unit having;
            computer processor,
            computer memory,
            plurality of digital signal input/output ports, and
            analogue to digital signal converter,
         means for releasably securing said core unit to said first detector module,
         detector member,
         a thermally insulated enclosure, said detector member being mounted within said thermally insulated enclosure,
         detector member analyte inlet member,
            said capillary column analyte outlet member being in fluid communication with detector module inlet member.

2. The trans-configurable modular chromatograph of claim 1, wherein a plurality of said first detector module's first computer processing unit's plurality of digital signal input/output ports are in digital signal communication with a plurality of said core unit's first computer processing unit's plurality of digital signal input/output ports, and a plurality of said first column module's first computer processing unit's plurality of digital signal input/output ports are in digital signal communication with a plurality of said core unit controller module's plurality of digital signal input/output ports.

3. The trans-configurable modular chromatograph of claim 1, wherein said means for switching stream flow from said first analyte stream conduit to and between at least one column module and at least one detector module is a "Y" fluid connector.

4. The trans-configurable modular chromatograph of claim 3, wherein said means for switching stream flow from said first analyte stream conduit to and between at least one column module and at least one detector module is an electro-mechanical or pneumato-mechanical switch.

5. The trans-configurable modular chromatograph of claim 3, wherein said means for switching stream flow from said first analyte stream conduit to and between at least one column module and at least one detector module is a Dean's switch.

6. The trans-configurable modular chromatograph of claim 1, further comprising
   d—second column module, said second modular unit having
      first computer processing unit,
         said first computer processing unit having;
            computer processor,
            computer memory,
            plurality of digital signal input/output ports,
         means for releasably securing said core unit to said second column module,
         capillary column,
         capillary column heater member,
         capillary column analyte inlet member,
      capillary column analyte outlet member,
         at least one of said capillary column analyte inlet member and outlet member being in fluid communication with said means for switching stream flow from said first analyte stream conduit to and between at least one column module and at least one detector module, and
      means for sensing and controlling the temperature of said capillary column.

7. The trans-configurable modular chromatograph of claim 1, further comprising e—second detector module, said second detector module having
  first computer processing unit,
    said first computer processing unit having;
    computer processor,
    computer memory,
    plurality of digital signal input/output ports, and
    analogue to digital signal converter,
  means for releasably securing said core unit to said second detector module,
  detector member,
  detector member analyte inlet member,
  said second detector module inlet member being in fluid communication with said means for switching stream flow from said first analyte stream conduit to and between at least one column module and at least one detector module.

8. The trans-configurable modular chromatograph of claim 6, further comprising
e—second detector module, said second detector module having
  first computer processing unit,
    said first computer processing unit having;
    computer processor,
    computer memory,
    plurality of digital signal input/output ports, and
    analogue to digital signal converter,
  means for releasably securing said core unit to said second detector module,
  detector member,
  detector member analyte inlet member,
  said second detector module inlet member being in fluid communication with said means for switching stream flow from said first analyte stream conduit to and between at least one column module and at least one detector module.

9. The trans-configurable modular chromatograph of claim 8, wherein a plurality said first detector module's first computer processing unit's plurality of digital signal input/output ports are in digital signal communication with a plurality of said core unit's first computer processing unit's plurality of digital signal input/output ports, and a plurality said first column module's first computer processing unit's plurality of digital signal input/output ports are in digital signal communication with a plurality of said core unit controller module's plurality of digital signal input/output ports.

10. The trans-configurable modular chromatograph of claim 9, wherein said core unit first heater member comprises a plurality of parallel radiation fins and heating means for heating said plurality of parallel radiation fins,
  a fan member, said fan member being within said core unit thermally insulated first enclosure, and being positioned to distribute heat within said thermally insulated first enclosure housing, and isothermally heat said first analytes stream inlet, and said first analyte stream conduit.

11. The trans-configurable modular chromatograph of claim 9, further comprising means for switching analyte stream flow between said first analyte stream conduit and at least two capillary columns and at least two detector modules.

12. The trans-configurable modular chromatograph of claim 9, wherein said core unit thermally insulated first enclosure, comprises an outer sheet metal enclosure, insulating means, and an inner sheet metal enclosure, said insulating means being enclosed between said outer sheet metal enclosure and said inner sheet metal enclosure.

13. The trans-configurable modular chromatograph of claim 9, wherein said column is spirally wound on a ring support, and further comprising a thermal resistive member substantially coextensive with said column, said thermal resistive member and said column member being enclosed within a sheath member, and means to maintain said thermal resistive member at a temperature equal to or above the maximum column operating temperature.

14. The trans-configurable modular chromatograph of claim 13, wherein said ring member is a high thermal conductivity metal.

15. The trans-configurable modular chromatograph of claim 14, wherein said high thermal conductivity metal is aluminum, copper or brass.

* * * * *